United States Patent [19]
Jain et al.

[11] Patent Number: 5,955,084
[45] Date of Patent: Sep. 21, 1999

[54] PROCESS FOR THE SIMULTANEOUS PRODUCTION OF ARTEMISNIN AND ESSENTIAL OIL FROM THE PLANT ARTEMISIA ANNUA

[76] Inventors: Dharam Chand Jain, Phytochemical Technology Division, Central Institute of Medicinal and Aromatic Plants PO-CIMAP; Sudeep Tandon, Chemical Engineering Division Central Insitute of Medicinal and Aromatic Plants, PO-CIMAP; Rajendra Singh Bhakuni; Mohammed Shafique Siddique, both of Phytochemical technology Division Central Institute of Medicinal and Aromatic Plants, PO-CIMAP; Atul Prakash Kahol, Chemical Engineering Division Central Institute of Medicinal and Aromatic Plants, PO-CIMAP; Ram Prakash Sharma, Phytochemical Technology Division, Central Institute of Medicinal and Aromatic Plants, PO-CIMAP; Sushil Kumar, Director Central Institute of Medicinal and Aromatic Plants, PO-CIMAP; Asish Kumar Bhattacharya, Phytochemical Technology Division Central Institute of Medicinal and Aromatic Plants, PO-CIMAP, all of Lucknow-226015, India

[21] Appl. No.: 08/944,865

[22] Filed: Oct. 6, 1997

[30] Foreign Application Priority Data

Mar. 17, 1997 [IN] India ................... 652/DEL/97

[51] Int. Cl.$^6$ .................................................... A61K 35/78
[52] U.S. Cl. ........................................................ 424/195.1
[58] Field of Search .......................... 549/299; 424/195.1

[56] References Cited

PUBLICATIONS

Woerdenbag et al., "Artemisinin, Related Sesquiterpenes, and Essential Oil in Artemisia annua During a Vegetation Period in Vietnam" *Planta Med.* 60:272–275 (1994).

Vonwiller et al., "An Improved Method for the Isolation of Qinghao (Artemisinie) Acid from Artemisia Annua" *Planta Med.* pp. 562–563 (1993).

Klayman et al., "Isolation of Artemisinin (Qinghaosu) from Artemisia Annua Growing in the United States" *Journal of Natural Products* 47:715–717 (1984).

Roth, "A Facile Semisynthesis of the Antimalarial Drug Qinghaosu" *J. chimical Education* 68:612 (1991).

*Primary Examiner*—Amelia Owens
*Attorney, Agent, or Firm*—Foley & Lardner

[57] ABSTRACT

This invention relates to a novel process for the dual production of essential oil and artemisinin from the plant Artemisia annua, said process comprising extracting the plant with hexane, partitioning the hexane extract between hexane and acetonitrile, hydrodistillation of hexane residue and Marc to yield essential oil, further fractionation of acetonitrile solvent between hexane-benzene mixture to remove artemisinic acid, chromatographing of the acetonitrile phase to produce substantially pure artemisinin, the artemisinic acid is reduced to obtain dihydro artemisinic acid which is then oxidised in a single step to form artemisinin.

19 Claims, 1 Drawing Sheet

PROCESS FOR THE SIMULTANEOUS PRODUCTION OF ARTEMISNIN AND ESSENTIAL OIL FROM THE PLANT ARTEMISIA ANNUA

FIELD OF THE INVENTION

The present invention relates to a process for the simultaneous production of essential oil and artemisinin from the plant *Artemisia annua*. More particularly, the invention is related to a process for the production of essential oil and artemisinin and conversion of artemisinic acid into artemisinin.

BACKGROUND OF THE INVENTION

*Artemisia annua* L. (Asteraceae) is a herb of Asiatic and Eastern European origin that has been also naturalised in USA. This species is receiving considerable attention because of the antimalarial activity of artemisinin of formula (1) a sesquiterpene lactone endoperoxide which is present in its aerial parts. In clinical trials, mainly performed in southeast Asia, artemisinin and a series of semi-synthetic derivatives have been proved to be effective against Plasmodium parasites with resistance to the commonly used antimalarial drugs. Now, efforts are being made to make these drugs cheaply available worldwide. In addition, *A. annua* is valued for its essential oil which has characteristic sweet aroma. Its application in perfumery, cosmetics, aromatherapy and as an antimicrobial, dermatological, fungicidal agents may provide an additional market for essential oil.

Artemisinic acid of formula (2) is the bio-synthetic precursor of artemisinin, which are generally present in greater quantity that artemisinin in *A. annua* plant. Artemisinic acid can be converted into artemisinin in good yield, thereby artemisinin amount obtained directly from the plant is increased 3–4 folds.

PRIOR ART REFERENCES OF THE INVENTION

So far, no prior art literature has provided a method for the simultaneous isolation of artemisinin and essential oil from *A. annua* plant without destroying any of them. At present, the herb *A. annua* is processed for obtaining the essential oil by hydrodistillation method (Woerdenbag, H. J. ; Pras, N; Chen, N. G., Bang Bui-Thi; Bos, R., Uden Wim Van; Pham Van Y; Boi, N. V; Batterman, S. and Lugt. C. (1994), Artemisinin related sesquiterpenes and essential oil in *Artemisia annua*, during vegetation period in Vietnam, Planta Medica, 60, 272–75). In this process, the fresh herb and water are heated in Clevenger apparatus at 100° C. for 3–4 hrs. The steam distillate is condensed and essential oil is collected but in this process artemisinin gets destroyed. As artemisinin is a thermally labile compound, it gets decomposed during hydrodistillation .

In another process, to isolate artemisinin and other biogentic precursors, the dried plant material is extracted with non polar solvent (hexane), partitioning the hexane extract between hexane and acetonitrile, followed by chromatographying the acetonitrile phase over silica gel, elution with solvent afforded different fractions, which on concentration and crystallization yielded artemisinin, artemisinic acid, arteannuin B, but no essential oil is recovered in this process. Klayman, D. L. ; Lin, A. J. Acton, N; Scovill, J. P.; Hoch, J. M.; Michous, W. K.; Theoharidis, A. D. and Dobek, A. S. J. Nat. Prods. 47, (1984) 715. Another disadvantage in the above process is that the artemisinic acid being predominant, it tends to elute with artemisinin, thus affecting the purity of the desired compound.

An improved method for the isolation of artemisinc acid from *A. annua* plant (Vonwiller, S. C., Hayne, R. K, King, G. and Wang, H. Planta medica 59, 562–563 (1993) was reported. In this process, methanolic extract of *A. annua* were partitioned between water and ether solvent. Ether residue was treated with base to separate artemisinic acid fraction from artemisinin. The basic solution was neutralized and further methylation of residue stirring with acid. After methylation the same base extraction process was repeated to obtain artemisinic acid. The residue left after base extraction was chromatographed to obtain artemisinin which afforded 57% of yield. In this process, total extract was treated with base which destroyed some amount of artemisinin. The solvent namely ether used in the process is low boiling and highly inflammable.

Artemisinic acid is the most abundant metabolite of *A. annua* and its conversion to artemisinin would increase the yield of artemisinin. Roth, R. J and Acton, N., J. Chem. Edu. 68,612 (1991) have prepared dihydroartemisinic acid by using excess quantity of $NaBH_4$ and $NiCl_2 6H_2O$ in methanol. Dihydroartemisinic acid was photo-oxidised at (−) 78° C. in dichloro methane or at 0° C. in solvent acetone with methylene blue as photosynthesiser and oxygen was passed through the solution with irradiating with high intensity lamp. The solution was evaporated and the residue was taken up in the ether and filtered the solution to remove dye. The solvent was evaporated, residue was re-dissolved in pet. ether, containing a few drops of trifluoroacetic acid and the photolysate was left for four days to afford 17–30% artemisinin. In this process, photo oxidation was carried out at low temperature and also used number of solvents, chemical and process steps.

SUMMARY OF THE INVENTION

Figure 1A:
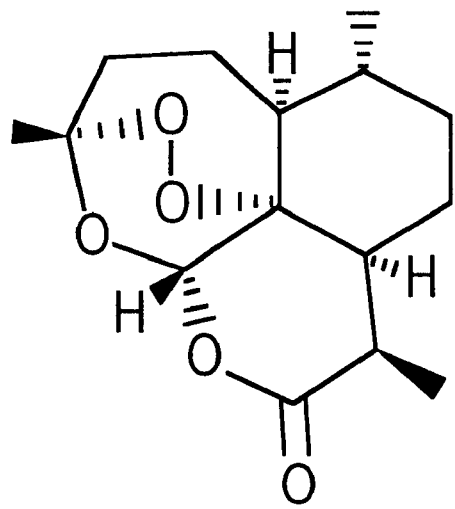
FIG. 1A shows the chemical formula 1 which is the chemical substance artemisinin.
Figure 1B:
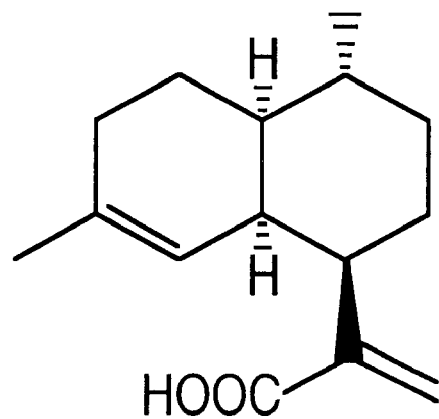
FIG. 1B shows the chemical formula 2, which is the chemical substance artemisinc acid.

The present invention provides a simple and efficient process for the simultaneous production of artemisinin and essential oil from the plant *A. annua* and also a method for better recovery of artemisinic acid and artemisinin without the use of chromatography and finally conversion of artemisinc acid into artemisinin.

NOVELTY OF THE INVENTION

1. In the prior art, essential oil is obtained by hydrodistillation of fresh/dried plant material in which artemisinin gets destroyed and the essential oil is obtained after 3 hrs. contact with steam, whereas in this present invention, the dried plant material is extracted with n-hexane and the extract is partitioned with aqueous acetonitrile. In this step, fatty material is seperated from artemisinin, so that purification and recovery of artemisinin is improved as well as essential is obtained by hydrodistillation of marc and hexane residue obtained in the partition step in which no artemisinin is present. Therefore, in this process, no loss of artemisinin takes place. For the first time, 50% essential oil is obtained from the marc of the plant. The quality of the oil is better and less time is required for hydrodistillation. For the first time, the applicants have achieved the simultaneous production of artemisinin and essential oil without destroying either of them.

2. In the previous process artemisinic acid was seperated from aqueous acetonitrile phase by the treatment with sodiumcarbonate or chromatography. In this process, artemisinin present also gets decomposed and only 57% artemisinin was recovered. But in the present invention, artemisinic acid will be seperated from artemisinin before treatment with base, so that both the compounds are recovered in 90% yield.

3. The conversion of artemisinic acid (obtained from *A. annua*) into artemisinin results in the best utilization of the compounds obtained during the process as well as increases the yield of artemisinin from the plant. As the synthesis of artemisinin is not economically viable plant remains the sole source for its large scale production. In the present improved process, conversion takes place in only two steps instead of the three steps as used in the prior art. The present process does not use any catalyst, photosynthesiser and oxygen. The reaction takes place at room temperature and work up of the reaction is very simple to obtain artemisinin.

SUMMARY OF THE INVENTION

The process of the present invention consists of the following steps:

(i) drying and powdering *A. annua* plant, (ii) extracting the said powdered herb of *A. annua* with hexane, (iii) reducing the hexane extract from step (ii) above to 5–20% of its original volume under vacuum;

(iv) partitioning the hexane extract between hexane and acetonitrile water mixture;

(v) evaporation of the hexane phase obtained in step (iv) to dryness, (vi) hydrodistillation of hexane residue from the step (v) and Marc (extracted plant material) to yield essential oil, (vii) removal of water from aqueous acetonitrile phase obtained from step (iv), (viii) further fractionation of resultant acetonitrile phase after removal of water as obtained from step (vii) between hexane-benzene mixture to obtain hexane-benzene extract and acetonitrile phase, (ix) treating hexane-benzene fraction obtained from step (viii) with a base followed by neutralization, extraction with chloroform, drying and crystallisation to obtain artemisinic acid, (x) converting artemisinic acid obtained from step (ix) into artemisinin by reduction and photo oxidation, (xi) chromatographying of the evaporating acetonitrile residue obtained from step (viii) over silica gel with hexane, (xii) evaporation of the different fractions obtained from step (xi) and crystallization of the said fractions containing artemisinin obtained from step (xi) and thereby producing substantially pure artemisinin.

DETAILED DESCRIPTION OF THE INVENTION

In accordance with the method of the invention, employing n-hexane solvent for extraction of the plant in which complete extraction of artemisinin and other bio-precursors and 50% of essential oil. The step of partitioning separates the fatty material from other products containing artemisinin, whereas defatting of crude extract with n-hexane, alcohol etc., results in the loss of artemisinin and filteration of fat is a difficult operation which is avoided in this process. In the previous process, the hydrodistillation of plant material to obtain essential oil, due to high temperature artemisinin gets destroyed during operations but here the applicants have separated the artemisinin fraction from fatty material which on hydrodistillation yield essential oil. In this process, the remaining essential oil in plant which is not extracted during hexane extraction which is to be identified and recovered from the extracted plant material (Marc) by hydrodistillation. The hydrodistillation of marc and concentrated hexane residue took less time and size of distillation unit is drastically reduced which is required during fresh plant extraction. During drying, the structure changes of the cells of plant material favour the diffusion of the oil components out of them.

The partitioning step in liquid-liquid extraction done in Karr type column at particular flow rate and stirring, transfer the artemisinin and two major sesquiterpene, in the acetonitrile phase (polar solvent) with concomitant reduction of in the amount of extract, i.e. of the order of 20–24% of the original hexane extract in the single operation.

The acetonitrile phase rich in artemisinic acid only 10% of the acid isolated by crystallization before chromatography. Here in this process, complete extraction or artemisinic acid by partitioning between acetonitrile and hexane-benzene mixture, which reduced the bulkness of the acetonitrile extract further by 50%. Using the method of the present invention, the second partitioning step which remove artemisinic acid prior to elution of artemisinin without chromatography, enhancing the purification of artemisinin, less consumption of silica gel, time and solvent and economize the cost of the drug-artemisinin. In the Vonwiller process, artemisinic acid was isolated from the ether extract by treatment with a base. In the ether extract, artemisinin which was also present get decomposed during the base extraction. Here the applicants have separated the artemisinic acid fraction from artemisinin.

In the chromatography step of the invention, ratio of (1:3)(solute to adsorbent) was discovered to yield excellent results. In the known process, a ratio of 1:10 has been required. In the solvent system of the invention, n-hexane was found to be quite effective rather than 10–20% ethyl acetate in n-hexane mixture. The silica gel used as a packing material in the example here is silica gel-H. (Mesh size-200). The elution of compounds done under reduced pressure. In this way elution of artemisinin by n-hexane rather than 15% ethyl acetate-hexane mixture, arteannuin B was covered by 5% ethyl acetate hexane mixture. By way of chromatography step of the process of elution, artemisinin was obtained from the oily greenish yellow fraction eluted with hexane and purification of artemisinin was carried by crystallization from ethyl acetate-hexane (1:4). In accordance with the description herein used, solvent, silica gel and time for chromatography reduced drastically.

Accordingly, the present invention provides a novel process for the simultaneous production of essential oil and artemisinin from the *Artemisia annua*, said process comprising (i) drying and powdering *A. annua* plant; (ii) extracting the said powedered herb of *A. annua* with hexane; (iii) reducing the hexane extract obtained from step (ii) above to 5–20% of its original volume under vacuum; (iv) partitioning the hexane extract between hexane and acetonitrile water mixture; (v) evaporation of the hexane phase obtained in step (iv) to dryness; (vi) hydrodistillation of hexane residue obtained from the step (v) and Marc (extracted plant material) to yield essential oil; (vii) removal of water from aqueous acetonitrile phase obtained from step (iv); (vii) further fractionation of resultant acetonitrile phase after removal of water as obtained from step (viii) with a base followed by neutralization, extraction with chloroform, drying and crystallization to obtain artemisinic acid; (x) converting artemisinic acid obtained from step (ix) into artemisinin by reduction and photo oxidation; (xi) chromatographying of the evaporating acetonitrile residue obtained from step (viii) over silica gel with hexane; (xii) evaporation of the different fractions obtained from step (xi) and crystallization of the said fractions containing artemisinin obtained from step (xi) and thereby producing substantially pure artemisinin.

The dried parts of the plant used for the extraction can be selected from any part of the plant, preferably leaves, infloroscence and small stems and the hexane extract of the A. annua as used in step (i) is reduced to 10% of its original volume under vacuum. Preferably, the partitioning between hexane and aqueous acetonitrile phase is done in the ratio of 2:3 in liquid-liquid extraction column and the aqueous acetonitrile mixture used is in the ratio of 1:1 to 1:5.

In the present process, the single extraction step (ii) is carried out between two phases for 3 hrs. and the hydrodistillation of Marc (extracted plant material) in step (i) and residue obtained from (iii) yield essential oil upto 2.0 hrs.

Also, in the present process, further partitioning between acetonitrile and hexane-benzene mixture after removal of water is done to isolate artemisinic acid and 10–30% benzene used in hexane solvent was used for the extraction of artemisinic acid.

Preferably, extraction of artemisinic acid is carried out where hexane-benzene mixture is evaporated, extracted with 5% of sodium carbonate solution and the basic solution is neutralized with 5% HCl solution, extracting with chloroform, drying the solvent and crystallization with ethyl acetate yielding artemisinic acid.

One embodiment of the invention provides a process for the conversion of artemisinic acid into artemisinin employing steps such as reduction and photo oxidation and the reduction is carried out by the following steps comprising (i) dissolving artemisinic acid and $NiCl_2.6h_2O$ in dry methanol; (ii) adding sodium borohydride to the resultant solution at 0° C. over a 2 hr. period; (iii) neutralising the solution obtained in step (ii) with 5% aqueous HCl solution and (iv) isolating and crystallizing the dihydro artemisinic acid in ethyl acetate to obtain pure dihydro artemisinic acid. However, the step of photo oxidation is carried out by comprising (i) dissolving the dihydroartemisinic acid in the solvent dichloromethane-ethyl acetate; (ii) oxidising the solution obtained in the step (i) in the presence of fluorescent light (40W) daily for two hours upto 8 days; (iii) concentrating the solution obtained in step (ii) and recrystallizing the residue in hexane to isolate artemisinin.

Preferably, in the present process, the chromatographic step is carried out in $SiO_2$ column comprising a solute having adsorbent ratio 1:3. The elution with n-hexane solvent is being done under vacuum at 100–150 mm Hg absolute pressure and the chromatographic absorbent used is Silica gel H with mesh size 200.

The process of invention is illustrated by the following examples which should not be construed to limit the scope of the present invention.

The following examples also illustrates the specific embodiments of the method of the invention.

EXAMPLE 1

Dried powdered herb of A. annua (40 kg) was percolated with hexane (60–80° C.) (6×200 liter) in a soxhlet for 8 hrs. The extracted solvent was reduced to 20 liter. The non polar phase (hexane extract) was partitioned with aqueous acetonitrile phase (1:5) presaturated each other in the liquid-liquid extraction (Karr type) column. After 3 hrs. two phases were separated. The aqueous acetonitrile phase was back washed using 10% of its separated. The aqueous hexane (2.0 litre). Evaporation of non polar phase provided (2.20 kg) residue. The residue was boiled in Clevenger apparatus with 10 litre water for 1.5 hrs, which yielded the essential oil (80 ml). The marc (extracted plant material) (40 kg) was hydrodistilled in a distillation unit, which yield essential oil (100 ml) in 1 hr. The water from aqueous acetonitrile phase was removed by adding 1 kg sodium chloride. The acetonitrile solvent (25.0 litre) was further partitioned between acetonitrile extract and 10% benzene-hexane mixture in the same karr type column. After separation of two phases, evaporated the benzene-hexane mixture yielded (200 gm) of residue. The residue (200 gm) was dissolved in chloroform (400 ml) and extracted with 5% $Na_2CO_3$, solution (3×500 ml). Basic solution was neutrilized with 10% HCl solution (400 ml). The neutral solution was extracted with chloroform, concentrated and crystallization with ehtylacetate yielded artemisinic acid (71.8 gm). The acetonitrile phase after concentration provide a residue (300 gm) which was filtered over silica gel (900 gm) under vacuum at 100–150 mm Hg absolute pressure. Artemisinin was obtained from the viscous greenish yellow fraction elutes with n-hexane. Purification of artemisinin was carried by recrystallization with ethyl acetate/hexane (1:4) to yield artemisinin (18 gm) Arteannuin B was obtained from the fraction eluted with 5% acetate in hexane. Evaporation of the fraction and crystallization yielded arteannuin B (36.5 kg).

The above procedure was repeated two times on the same scale and consistently provided the same yield of artemisinin and other constituents.

EXAMPLE 2

The process followed as in example 1 in which the organic phase (20 litre) was partitioned with aqueous acetonitrile phase (1:5, 30 litre) in same extraction column for the same period of time. The acetonitrile phase after removal of water was dried over anhydrous sodiumsulphate and concentrated under reduced pressure to yield a residue (0.55 kg). This residue was chromatographed over silica gel (2.5 kg) and eluted with different ratio of ethyl acetate-hexane. Artemisinin was obtained from column fractions eluted from 8% ethyl acetate-hexane. Evaporation and crystallization with hexane ethyl acetate mixture afforded pure artemisinin (18.0 gm) fraction eluted from 5% ethyl acetate hexane yielded artemisinic acid (70.6 gm) where as 12% ethyl acetate in hexane fraction afforded arteannuin B (35.8 gm).

EXAMPLE 3

The process of extraction of A. annua was followed as in example 1 in which the hexane phase (20 litre) was partitioned with aqueous acetonitrile phase (1:3, 30 litre) in same extraction column for the same period of time and speed. After partitioning the hexane phase was concentrated to yield (1.82 kg) residue which on hydrodistillation yielded essential oil (50 ml). The acetonitrile extract was concentrated after removal of water and yielded viscous mass (0.8 kg). This viscous mass was chromatographed over silica gel (4.0 kg) and eluted with different ratio of solvent ethyl acetate-hexane. Artemisinin was obtained from column fractions eluted with 10% ethyl acetate-hexane. Evaporation and crystallisation with hexane ethyl acetate mixture afforded pure artemisinin (17.0 gm).

EXAMPLE 4

Dried herb of *A. annua* (40.0 kg) was extracted with n-hexane in a soxhlet apparatus. The extracted solvent was reduced to 20 litre. The hexane soluble fraction (10 litre) was partitioned with aqueous acetonitrile phase (1:1, 30 litre) in same extraction column. The hexane soluble fraction obtained after partitioning was evaporated and residue (1.70 kg) was boiled in Clevenger apparatus with 8 litre water for 3 hrs. which yield the essential oil (40 ml). The acetonitrile phase was concentrated and yielded viscous mass (1.24 kg) which on chromatograph on silica gel as per example 3 yielded pure artemisinin (16.2 gm).

EXAMPLE 5

Artemisinic acid is isolated from *A. annua extract as in example* 1 was used for conversion into artemisinin. Artemisinic acid (100 mg) was dissolved in 100 ml methanol containing 150 mg $NiCl_2.6H_2O$, 300 mg of $NaBH_4$ powder was added in small portions over 2 hr. period to a stirred and cooled solution. After the reaction was completed, excess reducing agent was destroyed by adding 20 ml of 5% aqueous HCl. The mixture was filtered to remove the insoluble impurities and then the aqueous methanolic solution was extracted with ether which was washed with water, dried and concentrated to afford 105 mg of crude dihydroartemisinic acid. Dihydroartemisinic acid (100 mg) was dissolved in dichloromethane-ethyl acetate (7:3, 20 ml), and the reaction mixture was left for 8 days at room temperature and irradiated with fluorescent light (tubelight) (40W) for a period of 2 hrs. per day. Solvent was removed under vacuum and the residue was recrystallized with n-hexane to afford artemisinin (25%.

The new process of production of essential oil and artemisinin, the subject matter of this patent, offered a number of advantages such as:

1. The process for the dual production of artemisinin and essential oil (80%) from *A. annua* has been developed for the first time.

2. Consumption of silica gel has decreased due to reduction of charging material upto 10% of its original hexane extract and ratio of adsorbent to solute is (1:3).

3. The partitioning step between n-hexane and aqueous acetonitrile phase allowed the selective transfer of artemisinin and other sesquiterpenes into polar phase leaving non polar constituents in hexane solvent which results in a better method for the removal of large quantity of fat and other impurities, whereas removal of fats is difficult operation.

4. Hydrodistillation of extracted plant and hexane residue is a better alternative to recover major portion of the essential oil than hydrodistillation from fresh herb where artemisinin gets destroyed.

5. In this process, after recovery of essential oil from hexane residue, the applicants also obtained major fatty acids material which on further purification yield free fatty acids.

6. Isolation of artemisinic acid without chromatography, as by product, can be converted into artemisinin which will increase overall yield of the artemisinin from the plant by 2–3 folds.

7. Conversion of artemisinic acid into artemisinin in two simple steps without using catalyst, dye, few solvents and oxygen. The present reaction takes place at room temperature.

8. The process is highly efficient and economical as most of the solvents and adsorbents used in the process are being recovered and reused.

9. All these advantages are significant economic value for large scale production of antimalarial drug artemisinin.

We claim:

1. A process for the simultaneous production of essential oil and artemisinin from the *Artemisia annua*, said process comprising
    (i) drying and powdering an *A. annua* plant part to produce a dried and powdered plant or plant part,
    (ii) extracting the powdered plant or plant part of *A. annua* with hexane to produce a hexane extract and a residual Marc.
    (iii) reducing the hexane extract to 5–20% of its original volume under vacuum,
    (iv) partitioning the resultant concentrated hexane extract between hexane and acetonitrile water mixture to produce a hexane phase and an aqueous acetonitrile phase,
    (v) evaporating the hexane phase to dryness to obtain a hexane residue,
    (vi) hydrodistilling the hexane residue and residual Marc to yield essential oil,
    (vii) removing water from the aqueous acetonitrile phase to produce an acetonitrile phase,
    (viii) extracting the acetonitrile phase with a hexane-benzene mixture to obtain a hexane-benzene extract and a residual acetonitrile phase,
    (ix) removing the hexane-benzene solvent to yield a residue
    (x) dissolving the residue in chloroform
    (xi) extracting the chloroform solution with a base,
    (xii) neutralizing the aqueous basic solution,
    (xiv) extracting the neutralized aqueous solution with chloroform,
    (xiv) evaporating the chloroform and crystallizing the extracted hexane-benzene extract to produce artemisinic acid,
    (xv) reducing and photooxidizing the artemisinic acid,
    (xvi) chromatographing the acetonitrile phase over silica gel with hexane and collecting different eluted fractions,
    (xvii) evaporating the different eluted fractions crystallizing said fractions to produce substantially pure artemisinin.

2. A process claimed in claim 1, wherein dried parts of the plant used for the extraction are selected from any part of the plant.

3. A process as claimed in claim 1 wherein partitioning between hexane and acetonitrile water mixture used in step (iv) is done in the ratio of 2:3 in liquid-liquid extraction column.

4. A process as claimed in claim 1 wherein acetonitrile water mixture used in step (iv) is in the ration of 1:1 to 1:5.

5. A process as claimed in claim 1 wherein partitioning step (iv) is carried out between two phases for 3 hrs.

6. A process as claimed in claim 1, wherein the time taken for hydrodistillation of Marc ranges between 30 minutes to 120 minutes.

7. A process as claimed in claim 1, wherein the hexane residue is hydrodistilled for 30 minutes to 120 minutes to obtain the essential oil.

8. A process as claimed in claim 1 wherein fractionation between acetonitrile and hexane-benzene mixture after removal of water in step (viii) is done to isolate artemisinic acid.

9. A process as claimed in claim 1 wherein benzene used in hexane-benzene mixture used as solvent ranges between 10–30%.

10. A process as claimed in claim 1, wherein the base used in step (ix) is a 5% solution of sodium carbonate.

11. A process as claimed in claim 1 wherein basic solution in step (ix) is neutralized with 5% HCl solution, extracted with chloroform followed by drying of solvent and crystallisation with ethyl acetate yielding artemisinic acid.

12. A process as claimed in step (x) of claim 1, wherein reduction in step (x) comprises (i) dissolving artemisinic acid and $NiCl_2.6H_2O$ in dry methanol; (ii) adding sodium borohydride to the resultant solution at 0° C. over a 2 hr. period; (iii) neutralising the solution obtained in step (ii) with 5% aqueous HCl solution and (iv) isolating and crystallizing the dihydro artemisinic acid in ethyl acetate to obtain pure dihydro artemisinic acid.

13. A process as claimed in claim 1, wherein the photo oxidation comprises (i) dissolving the dihydro artemisinic acid in dichloromethane—ethyl acetate solvent; (ii) oxidising the solution obtained in step (i) in the presence of fluorescence light daily for two hours up to 8 days; (iii) concentrating the solution obtained in step (ii) and recrystallizing the residue in hexane to isolate artemisinin.

14. A process as claimed in claim 1 wherein the chromatographic step is carried out in $SiO_2$ columns comprises a solute having adsorbent ration 1:3.

15. A process as claimed in claim 1 wherein the elution with n-hexane solvent is being done under vacuum at 100–150 mm Hg absolute pressure.

16. A process as claimed in claim 1 wherein chromatographic adsorbent used is Silica gel H with mesh size of about 200.

17. A process for the simultaneous production of essential oil and artemisinin from the plant *A. annua* wherein the yield of essential oil obtained from the marc of the plant is about 50%.

18. A process for the simultaneous production of essential oil and artemisinin from the plant *A. annua* wherein artemisinic acid and artemisinin are recovered in about 90% yield.

19. A process as claimed in claim 2, wherein the dried part of the plant is selected from the group consisting of leaves, infloroscence and small stems.

* * * * *

UNITED STATES PATENT AND TRADEMARK OFFICE
CERTIFICATE OF CORRECTION

PATENT NO.   :   5,955,084
DATED        :   September 21, 1999
INVENTOR(S)  :   Dharam Chand JAIN, et al.

It is certified that error appears in the above-identified patent and that said Letters Patent is hereby corrected as shown below:

On the title page, Insert --[73] Assignee: COUNCIL OF SCIENTIFIC & INDUSTRIAL RESEARCH, New Delhi, India--.

Signed and Sealed this

Thirty-first Day of October, 2000

Attest:

Q. TODD DICKINSON

*Attesting Officer*   *Director of Patents and Trademarks*